United States Patent [19]
Glad et al.

[11] Patent Number: 5,772,665
[45] Date of Patent: Jun. 30, 1998

[54] DEVICE FOR MIXING A PHARMACEUTICAL COMPOSITION WITH AN OTHER AGENT

[75] Inventors: Håkan Lars Christer Glad, Åsa; Tore Anders Kers, Södertälje; Mats Anders Rudén, Askim, all of Sweden

[73] Assignee: Astra Aktiebolag, Sodertalje, Sweden

[21] Appl. No.: 970,235

[22] Filed: Nov. 14, 1997

Related U.S. Application Data

[63] Continuation of Ser. No. 360,797, filed as PCT/SE95/0096, Oct. 24, 1994, published as WO95/12424, May 11, 1995, abandoned.

[30] Foreign Application Priority Data

Nov. 3, 1993 [SE] Sweden ............................. 9303630.9
Mar. 25, 1994 [SE] Sweden ............................. 9401010

[51] Int. Cl.$^6$ ............................................. A61M 37/00
[52] U.S. Cl. ........................... 604/82; 604/85; 604/187; 604/191; 604/213; 604/231; 604/236; 604/89
[58] Field of Search ............................. 604/82, 85, 187, 604/191, 213, 231, 236, 89

[56] References Cited

U.S. PATENT DOCUMENTS

| | | | |
|---|---|---|---|
| 4,898,580 | 2/1990 | Crowley | 604/191 |
| 5,067,948 | 11/1991 | Haber et al. | 604/213 |
| 5,069,670 | 12/1991 | Vetter et al. | 604/82 X |
| 5,181,918 | 1/1993 | Brandhorst et al. | 604/187 X |

FOREIGN PATENT DOCUMENTS 0323109  7/1989  European Pat. Off. .

*Primary Examiner*—Michael Powell Buiz
*Assistant Examiner*—N. Kent Gring
*Attorney, Agent, or Firm*—White & Case L.L.P.

[57] ABSTRACT

Device for mixing a pharmaceutical composition stored in a chamber (44) in said device with an agent to be added shortly before administration to form a preparation to be adminstered. The device should be capable of being shaken without leaking. It comprises a hollow body (2) having an outlet (4) sealed by a removable closure (12) and a plunger (6), which is slidable therein in sealing contact with the inner wall of the hollow body (2). The plunger (6), the hollow body (2) and the removable closure (12) define said chamber (44). An actuating means (22) is connected to the plunger (6) for displacing the same in the hollow body (2). A filling conduit (19) for said agent is connected to the chamber (44). A check valve (30) is associated with the conduit (19) and the chamber (44), which prevents flow from the chamber (44) but permits flow into said chamber through said conduit (19). A process for preparing a pharmaceutical preparation and a method for administration of said preparation with the device are also disclosed.

14 Claims, 3 Drawing Sheets

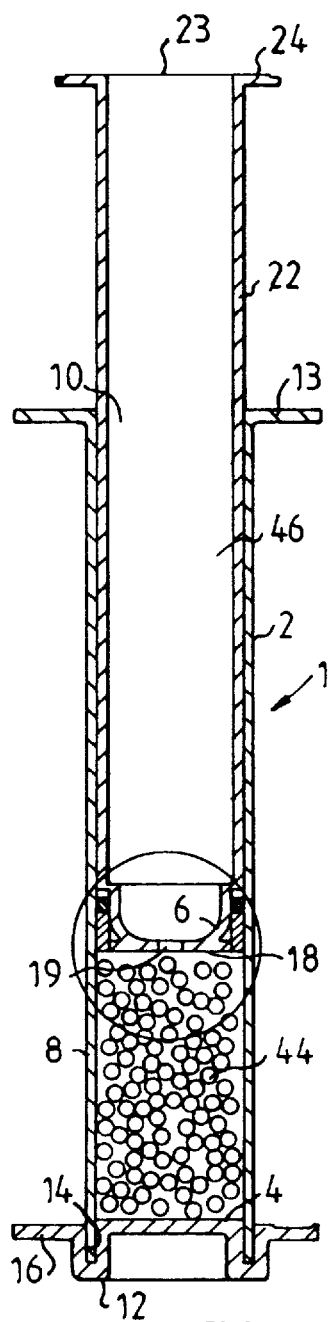
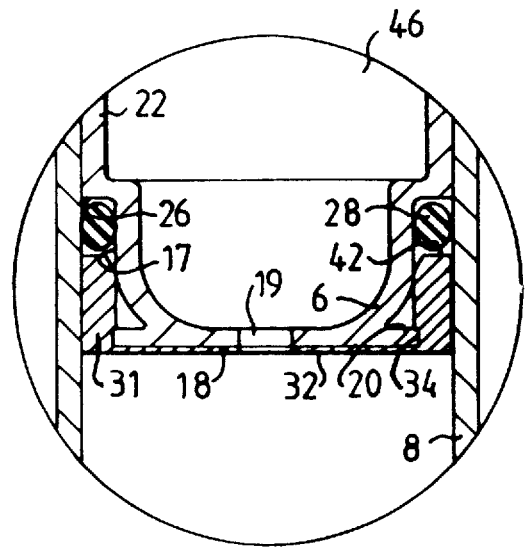
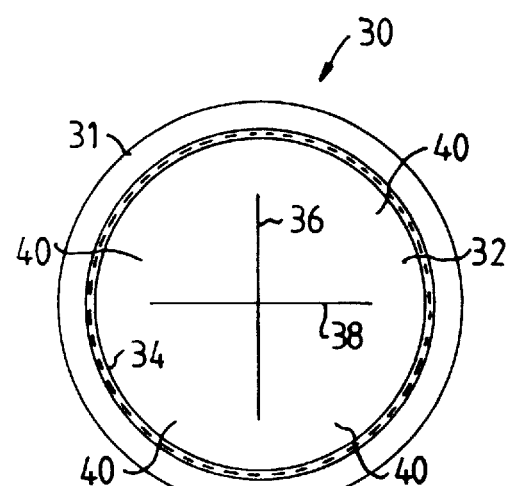

5,772,665

DEVICE FOR MIXING A PHARMACEUTICAL COMPOSITION WITH AN OTHER AGENT

This applicaton is a continuation of application Ser. No. 08/360,797, filed as PCT/SE94/00996, Oct. 24, 1994 published as WO95/12424, May 11, 1995 now abandoned.

TECHNICAL FIELD

The invention relates to a device for mixing a pharmaceutical, preferably dry and granular, composition, with another, preferably fluid, agent to a preparation, preferably a gel, in accordance with the preamble of claim 1. Furthermore the invention relates to processes for preparing a pharmaceutical preparation and methods for administering the preparation to a living being.

BACKGROUND OF THE INVENTION

The major problem forming the basis for the present invention relates to the handling, the storage and the administration of a pharmaceutical composition to be mixed with another agent, that may adversely affect the stability of the composition to form a preparation suited for administration to a living being, especially an animal.

It is well known in the veterinary art to administer pharmaceutical compositions in the form of paste-like preparations to horses by means of a syringe-like device. The syringe is then inserted into the mouth of the horse and the preparation is expelled onto the root of the tongue. The viscous nature of the preparation and the placing thereof in the back of the mouth makes it difficult for the horse to spit out the preparation.

In some cases such preparations, e.g. comprising a mixture of a pharmaceutical composition and a consistency forming agent, will have a short storage stability. Therefore, the components comprised in those preparations must be kept isolated from each other until a short time before use, when they are mixed with each other to form the desired preparation.

There exists a plurality of solutions to the problem of storing and mixing two components to a preparation, which can not be stored for a longer period of time after mixing.

The most common prior solution is a syringe of the kind disclosed in the U.S. Pat. No. 3,340,873, having a plunger, slidably accomodated in a cylindrical body. The two components to be mixed are contained in two different compartments, isolated from each other by a thin diaphragm. Shortly before the preparation is to be used, the diaphragm is ruptured or pierced, so that a communication is established between the two compartments. The syringe, with the mixture is then shaken to form a homogenous preparation. After this operation a cap is removed to open a passage and the content is expelled through a needle by depressing the plunger.

This kind of prior art has in most cases proved satisfactory and reliable and is moreover relatively easy to manufacture, e.g. by plastics injection molding, at a low cost.

However, the above syringe is not suitable for the administration of a gel, primarily because of the presence of the needle. But apart from this, generally, mixing devices having two compartents isolated from each other by a thin diaphragm of rubber or plastics could not be used for certain kinds of moisture sensitive pharmaceutical compositions. An example of such a composition is omeprazole, which degrades during long term storage in the presence of moisture. The always present molecular migration through a rubber or a plastics diaphragm would be sufficient to cause degradation of such sensitive compositions during long term storage.

Thus, conventional two compartments mixing devices are unsuitable for such compositions.

DK Patent Specification 112 893 filed Jul. 25, 1966, discloses an injection syringe for the injection of a pharmaceutical composition, that can not be stored in solution for a longer period of time without detrimental effects. The syringe basically corresponds to a standard syringe, the main difference being that the opening in the needle fitting is sealed by a diaphragm. The composition is contained in the syringe in dry form. When the syringe is to be used, a double ended injection needle is mounted on the needle fitting, one end of the needle piercing the diaphragm. Solvent is aspirated into the syringe through the needle. Then the syringe is shaken and the resulting solution is injected through the needle.

A drawback with this type of syringe is that the filling operation is rather complex, it requires the mounting of a double-ended injection needle for piercing the diaphragm. Furthermore, after the rupture of the diaphragm, the mixing chamber will be open to the air, so that care must be taken during the shaking operation to prevent the mixture from leaking out through the needle. Further, because of the high flow resistance of the syringe due to the narrow passages therein, in particular in the needle, it could not be used for viscous, pasty or gel-like preparations. Moreover, this known apparatus is not suited for oral administration because of the needle. Furthermore, the manufacturing costs for the syringe will be relatively high.

OUTLINE OF THE INVENTION

An object of the invention is to obviate the disadvantages of the prior art by providing a mixing device, in which a pharmaceutical composition may be stored for a longer period of time and to which a desired agent easily and rapidly can be added immediately before the administration of the preparation. After addition of the agent the device also should be capable of being vigourously shaken without leaking. Furthermore, the manufacturing cost for the device of the invention should be relatively low.

This object of the invention is attained at by a device in accordance with the preamble of claim 1, which includes the features of the characterizing part of claim 1.

Further independent claims define processes using the device for mixing a pharmaceutical preparation and methods for administration of a mixed preparation by means of the device.

When to be used for administration of the preparation, a package or a seal which protects the prefilled chamber against moisture during storage first has to be removed. After the removal of possible conduit seals, the conduit is brought in communication with a supply of the preferably fluid agent. Then the plunger is displaced in opposite direction to the expel direction causing an expansion of the closed chamber defined by the plunger, the axial side wall portion and the closure, thereby creating a vacuum in the chamber. In the beginning the pressure differential over the check valve will be too low to open it, but when the plunger has been displaced a sufficient distance, the pressure within the chamber will be sufficiently low to open the check valve. The agent will then be aspirated from the conduit into the chamber. When the required amount of agent has been drawn into the chamber the device is vigourously shaken until the preparation is ready for administration. Just before the administration is to be carried out, the closure to the chamber is removed and the device is inserted in for example the mouth of a horse. The content of the device is now expelled by depressing the plunger.

DESCRIPTION OF PREFERRED EMBODIMENTS

Preferred embodiments of the invention will now be described by way of example with reference to the drawings, in which:

FIG. 1 is an axial section of a first preferred embodiment of the invention,

FIG. 2 shows the encircled portion in FIG. 1 at a larger scale, and

FIG. 3 is a top view at a larger scale of a diaphragm, which constitutes an essential part of the embodiment shown in FIG. 1.

Figure 4:
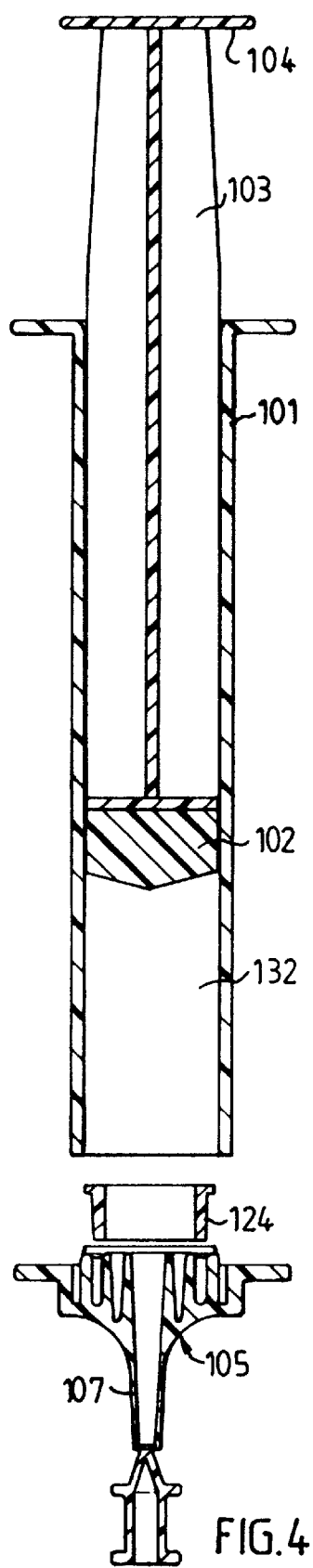
FIG. 4 is an axial section of a second preferred embodiment of a device according to the invention.
Figure 5:
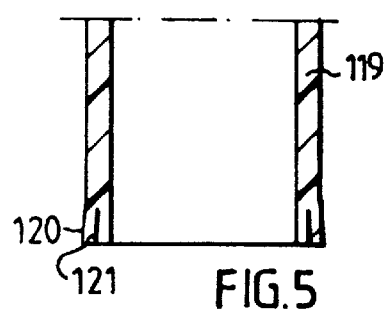
FIG. 5 is an enlarged view of the end of a tubular housing of the device in FIG. 4.
Figure 6:
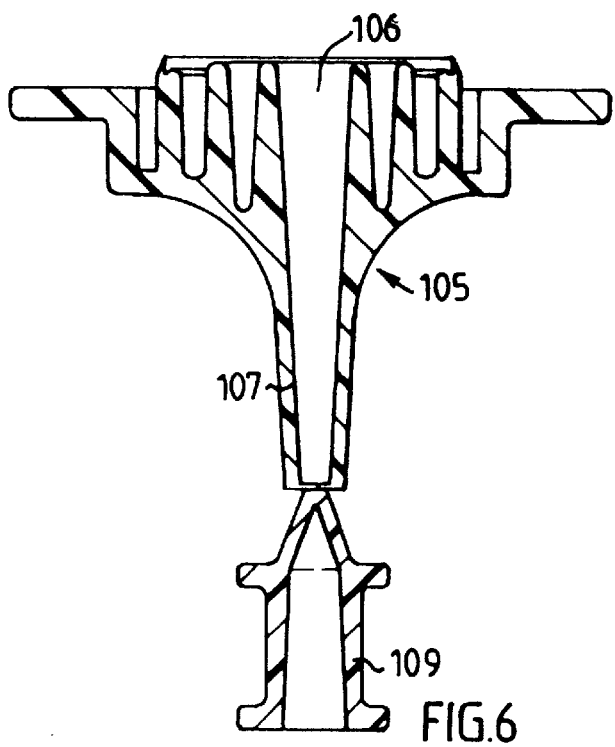
FIG. 6 is a section through a plug-like element for sealing the end of the tubular housing of FIG. 5, FIGS. 7 and 8 show enlarged details of the element shown in FIG. 6.

As shown in FIG. 1, the syringe-like device 1 of the first preferred embodiment of the invention, comprises a tubular, elongated, cylindrical hollow body 2, which is open at both ends. The lower end in FIG. 1 is the outlet end 4. The plunger 6 is inserted through the upper end 10. A flange portion or a finger grip portion 13 extends substantially perpendicular to the longitudinal direction of the hollow body 2 around the upper end thereof. The outlet end 4 is closed by a removable lid 12, which has a groove 14, having a diameter corresponding to that of the side wall 8 of the hollow body 2. The groove 14 is constructed with a depth to provide an airtight seal with the lower end 4 of the cylindrical body into the interior of the hollow body 2. The lid 12 has a radially extending flange portion 16 to facilitate the removal of the lid 12 when the preparation is to be expelled.

The plunger 6 is accomodated in the hollow body 2 in sealing contact with the side wall 8. It comprises an axially extending, substantially cylindrical portion 17, which passes over in a radial planar end wall 18. An axial through passage 19, is provided in the end wall 18, the axis of which coincides with the axis of the hollow body 2. The end wall 18 comprises an annular projection 20, which extends beyond the external surface of the cylindrical portion 17 in the radial direction.

A rod 22 is made integral with the plunger 6. Its external diameter is somewhat smaller than the internal diameter of the hollow body 2, so that the rod 22 is slidable therein. The rod 22 is tubular, the interior of which constitutes a compartment 46 in communication with the passage 19. At the open end 23 of the rod 22 a radially extending finger grip 24 is provided. The external diameter of the cylindrical portion 17 of the plunger 6 is considerably smaller than that of the rod 22, thus leaving an annular shoulder 26 in this area. The shoulder 26 constitutes an upper axial abutment for a sealing means in the form of an O-ring 28. The O-ring 28 is slightly compressed between the side wall 8 of the hollow body 2 and the circumferential surface of the plunger 6 to isolate the space above the O-ring 28 from that below the same.

Finally, the plunger 6 supports a diaphraghm member 30 which comprises a thick and relatively rigid substantially cylindrical, axially extending portion 31. Integral with the lower part of said portion 31 is a thin circular, radially extending and slitted diaphragm 32. The upper part of the cylindrical portion constitutes a lower axial abutment 42 for the O-ring 28. Immediately above the diaphragm 32, the cylindrical portion 31 comprises an annular groove 34, the width of which is about the same as the thickness of the annular projection 20 of the plunger 6, the diameter of the annular groove 34 being slightly smaller than the external diameter of the projection 20.

The diaphragm 32 is made of a resilient material and includes two slits 36, 38, perpendicular to each other, so as to form four identical flaps 40, which will deflect, when subjected to a sufficiently large force and return to their original position upon the removal of said force. When the lid 12 or other seal is placed on the outlet end 4, a closed chamber 44 is defined by the lid 12 or other seal, the diaphragm member 30, the O-ring 28 and the side wall 8, the volume of said chamber 44 being variable due to the axially displaceable plunger 6, which supports the O-ring and the diaphragm member 30.

During assembly, the O-ring 28 is first pushed onto the plunger 6, then the diaphragm member 30 is placed thereon and displaced in the axial direction until the annular groove 34 is brought into engagement around the projection 20. In this position the thin diaphragm 32 lies very closely to or rests against the end wall 18 of the plunger 6. Thus, in this position the flaps 40 can not deflect upwardly, thereby preventing flow from the lower side through the diaphragm 32. On the other hand, if there is a sufficient pressure differential over the diaphragm 32, with the lower pressure present on the lower side thereof, then the flaps 40 will bend downwardly leaving an opening in register with the passage 19 in the plunger 6 end wall 18, so that flow can take place from above the diaphragm 32 into the chamber 44.

Thus, the diaphragm 32 together with the end wall 18 function as a check valve or a non return valve.

The function of this first embodiment of the device will now be described by way of an example. In the following example the pharmaceutical composition is constituted by beads of an active substance, such as enteric coated pellets of omeprazole mixed with a gelforming agent such as xanthan gum, guar gum, locust bean gum, tragacanth, modified cellulose derivates or similar, to which mixture of dry components, water later is added for forming a viscous gel, but of course the use of the device will not be restricted to this application:

A suitable dosage of a dry mixture of omeprazole pellets and a gelforming agent is filled into the chamber 44. A buffering or pH-adjusting agent such as citric acid may optionally be added to prevent premature dissolution of the enteric coated beads when water later is added to the composition. This operation could be carried out in two ways, either the plunger 6 is placed in a suitable position in the hollow body 2 with the lid 12 removed, the filling then taking place through the lower end 4, or the lid 12 is applied on the lower end 4 with the plunger 6 removed, the filling then taking place via the upper opening 10. The quantity or the volume of the mixture is optional within certain limits, since the volume of the chamber 44 is variable because of the axially displaceable plunger 6. When the filling is completed, the lid 12 or other seal is applied onto the end 4 or the plunger 22 inserted into the hollow body 2, respectively.

In view of the hygroscopic nature of the gelforming agent, and a required storage stability of several years, for the pharmaceutical composition, the content in the chamber 44 must be protected against penetrating moisture, which else would accumulate in the gelforming agent to sooner or later cause degradation of the omeprazole during long-term storage. Therefore, after the filling operation, the device is enclosed in a moisture tight envelope, preferably having a moisture barrier made of aluminium, but other materials fulfilling the same purpose are of course also conceivable. As an alternative to the above package, it might be sufficient providing an impermeable seal of a similar material on top of the open end 23 of the rod 22. The device could now be stored for several years until use.

When to be used, the device is taken out from the moisture tight package or the seal on top 23 of the tubular rod 22 is removed. A suitable quantity of water to be added to the mixture within the chamber 44 is then filled into the tubular compartment 46 of the rod 22 up to a desired level (preferably at least the tubular rod 22 is provided with gradation lines). The plunger 6 is then displaced upwardly, thus creating a vacuum in the chamber 44. After a sufficient displacement, the vacuum will be so strong therein, that the diaphragm 32 will open, so that the water in the compartment 46 of the rod 22 will be aspirated into the chamber 44 through the pasage 19. When the water has been transferred thereto, the device is shaken until a viscous gel containing the omeprazole pellets is formed. During the shaking operation, the check valve will be closed thus preventing back flow from the chamber 44 to the passage 19. The mixture could be stored in the device for a short period of time before administration. Just before administration the lid 12 is removed and the device is placed, where the preparation is to be administered. The preparation is then expelled by depressing the plunger 6.

Conveniently, the rod 22 has such an axial length, that when fully depressed, all of the preparation is expelled from the device.

Instead of the plastic lid 12, a tear-off or a rupturable seal could be provided to seal the chamber 44.

Referring now to FIGS. 4–10, and in particular FIG. 4, a second preferred embodiment of the device has the general configuration of an ordinary syringe comprising a tubular housing 101 which at one end is closed by a movable plunger 102, for instance made of synthetic rubber. The plunger 102 is attached to an actuating rod 103 provided with a handle 104. It should be noted that the rod 103 may be permanently attached to the plunger 102 or may be delivered separately and be attached to the plunger when the device is to be used. The actuating rod has a length which is sufficient to partly push the plunger out of the tubular housing.

Figure 7:
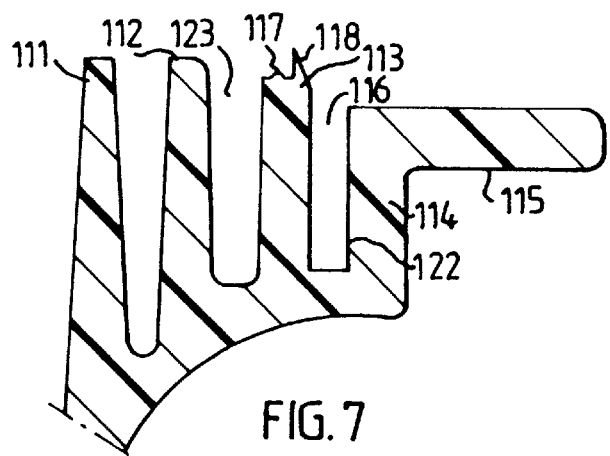
Figure 8:
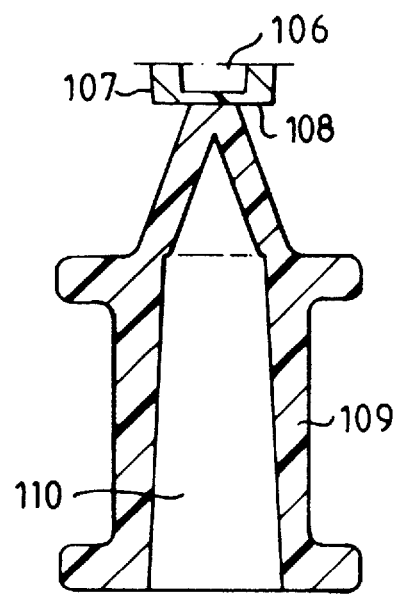

The opposite end of the housing 101 may be closed by a removable plug or closure 105 having a sealed opening 106 and provided with a male luer cone 107. The closure 105 is more clearly shown in FIGS. 6, 7 and 8. The cone 107 is sealed by means of an integrally moulded membrane 108 forming a frangible seal. An actuating tab 109 in the form of a cap with an interior, female luer cone 110 is integral with the membrane 108. As can be seen in FIG. 8, the tab 109 should be joined to the membrane 108 more or less centrally, leaving a part of the membrane between tab and cone around the entire periphery of the tab. The membrane can be ruptured by forcibly removing the tab 109, for instance tipping the tab 109 sideways. If so desired, the tab 109 can be turned around and used as a temporary cap on the male luer cone when the tab has been removed from the male luer cone 107. The male luer cone is provided so that a plastic container having a corresponding female luer cone, for instance a Polyamp™ ampoule, may be fitted onto the syringe, should it be desirable to use e.g. a sterile mixing liquid. If desired, a standard injection needle also can be fitted onto the luer cone 107 in order to allow the liquid to be taken from an ordinary standard ampoule made of glass or from a similar container.

The end of the closure 105 facing away from the male luer cone is provided with four circular flanges 111, 112, 113 and 114 extending generally along the longitudinal axis of the closure (and, in use, of the tubular housing 101). The two outermost (i.e. the third and fourth flanges) flanges 113 and 114 define a relatively deep groove 116 into which the end part 119 of the tubular housing 101 is to fit closely, i.e. so that a frictional fit is obtained. The groove 116 has a bottom part 122 that flares slightly outwardly in order to accomodate a portion 120 of the end part 119 which flares slightly outwardly (cf FIG. 5). The transverse end surface of the end part 119 is also provided with an axially oriented, circumferential slit 121. When the end part 119 of the tubular housing is pushed into the groove 116, the flaring portion 120 of the end part 119 can resiliently and sealingly engage the flaring part 122 in the groove. In this way a positive lock is obtained between the closure 105 and the tubular housing 101 in addition to the frictional fit or lock referred to above.

The outermost flange 114 also is provided with a radially oriented flange 115 extending in an orthogonal direction outwards from the device when the closure 105 is mounted on the tubular housing 101. This radial flange will facilitate the removal of the closure 101 from the tubular housing 101 when the device is to be used for administration of the preparation to a patient.

Figure 9:
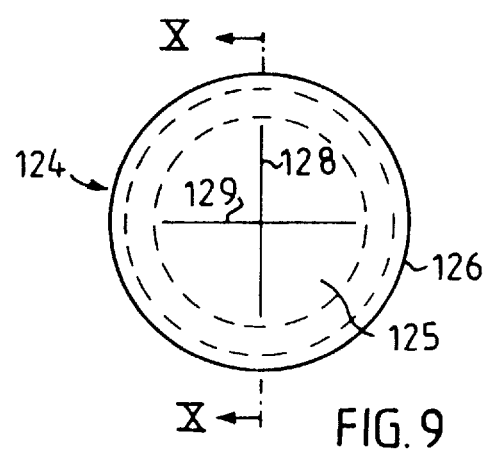
FIG. 9 is a top view of a non-return valve to be used in the device.
Figure 10:
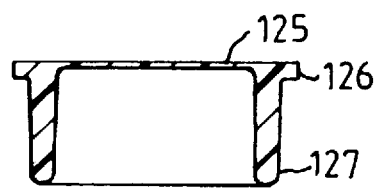
FIG. 10 is a section taken along the line X—X in FIG. 9.

The second and third flange 112 and 113 define a second groove 123 into which an annular, axially oriented flange 127 of a non-return valve 124, shown in detail in FIGS. 9 and 10, is to fit. The non-return valve 124 is also provided with a radially projecting edge or flange 126 intended to bear against an upright flange 118 and a bead 117 located on the edge of the third flange 113, which serves to support and to join the edge 126 to the flange 113 when the edge 126 is ultrasonically welded to the flange 113.

The non-return valve is provided with a relatively thin membrane 125 extending over the entire part of the valve located inside the flange 127. Similar to the first embodiment, the membrane is provided with two orthogonal slits 128 and 129 extending radially over almost the entire width of the membrane.

When the non-return valve has been welded to the flange 113, the membrane 125 will be located over and be supported by the two innermost flanges 111 and 112. As can be seen in FIG. 7, the flanges 111 and 112 are slightly higher than the flange 113, which results in the membrane 125 being tensioned over the flanges 111 and 112.

A more important effect of the presence of the flanges 111 and 112, the flange 111 in particular, is that the flaps of the membrane 125 being formed by the slits 128 and 129 are hindered from moving towards the opening 106, but are allowed to move in an inward direction when the closure 105 is mounted on the tubular housing 101. By these means the membrane will function as a simple but efficient non-return valve.

The operation of the second embodiment will now be described. A pharmaceutical composition e g of the same kind as that which is used in connection with the above description of the first embodiment of the device of the invention is filled into the tubular housing of the device, one end thereof being closed by the plunger 102. The plunger has then previously been displaced in the tubular housing to a position that for instance may be marked with a line on the tubular housing, leaving room for the dosis of the mixture later to be administered. After the filling operation through the open end 119, the tubular housing 101 is sealed by placing the closure 105 onto the open end 119. When the open end 119 reaches the bottom of the groove 116 of the closure, the flaring 120 of the end of the housing 101 will snap into engagement with the widened part 122 of the groove 116.

For long-time storage, the entire device suitably is placed in a airtight package or container.

When to be used, the device is taken out from the package and the tab 109 is removed together with the membrane 106. The now open tip of the closure 105 is then placed in a suitable solvent, in this case water and a predetermined amount of water is then drawn into the device by displacing the plunger upwardly (in FIG. 5) from its existing position to another position which also may be marked with a line, a stop or bead or similar means in the tubular housing. The water may be taken from any suitable source, for instance from a Polyamp™ ampoule. If needed, additional air may be drawn into the device, the tip of the closure then of course not being in contact with water.

The device is then shaken until the contents have been well mixed. The proportions between the gelling agent and the water are such that the resulting mixture remains in the device even after the removal of the plug.

The non-return valve is closed during the shaking operation then preventing leakage. It further prevents the dry composition from entering the opening 106 during the handling and storage of the device. This is important in view of the need of keeping the dose of the drug constant, without any losses through said opening upon removal of said frangile seal 108.

When the mixture is to be administered e g to a horse, the closure 105 is removed and the device is inserted into the mouth of the horse just in front of the first pre-molar tooth so that the end of the device will be located above the root of the tongue. The plunger is then displaced towards the open end, all the gel-like mixture in the device being deposited onto the root of the tongue (it should be noted that all of the mixture will be expelled after a complete plunger stroke). The mixture will be deposited so far into the mouth of the horse that it will be very difficult for the horse to spit out the preparation, and the horse consequently has to swallow the medication.

Of course both the first and second preferred embodiments of the invention can be modified in many ways within the scope of the appended claims. The actuating rod need for instance not be permanently attached to the plunger and may for instance be separately delivered together with the tubular device to be attached to the plunger when the device should be used.

The sealing contact between the hollow body and the plunger can be made as an integral part of the diaphragm or as a sealing means in the form of an O-ring.

The frangible seal need not be in the form of a membrane provided with an actuating tab and it could for instance be in the shape of an ordinary twist-off cap joined to the opening via a breaking line. It is also quite within the scope of the invention to use an ordinary removable cap or stopper, for instance made of rubber, to seal the opening in the plug.

It should also be noted that the syringe naturally also can be filled with dry composition through the end of the housing normally containing the plunger instead of being filled through the end containing the plug.

It should further be noted that in both embodiments all the elements can be made of polymeric materials, such as for instance polyethylene, polypropylene, polyester, rubber or silicone, and manufactured by conventional and cheap methods, such as injection moulding. Moreover, all the details have a simple construction and are easy to assemble. Consequently, the devices can be produced at a low cost.

Further modifications of the two embodiments could of course be made within the scope of the appended claims. In the described embodiments, for example, the slits of the diaphragm are oriented perpendicularly to each other and intersect each other in the centre of the diaphragm. However, it is quite possible to provide more than two slits. The slits may also be located offset from the mouth of the conduit, an unpierced part of the diaphragm then covering the conduit 19;106 when mounted on the plunger 6 or on the plug 105. Alternatively, openings located offset from the mouth of the conduit may not be of the slit type. When the plunger 6;102 has been displaced to create a sufficiently low vacuum in the chamber 44;132, the agent, water in the described embodiments, will be sucked through the conduit 19;106, which then will flow out laterally from the conduit along the diaphragm 30;124 towards the now open slits into the chamber 44;132.

One single slit offset disposed or in register with said conduit is also conceivable.

The check valve need not be of the diaphragm type. Any known kind of non return valves may be used in this connection provided that the valve material is compatible with the agents to be used.

In the above described embodiments of the invention the lid 12 and the closure 105 both are provided with an annular radially protruding flange, which extends around the whole circumference of the lid 12 and the closure 105, respectively and forms a grip portion for facilitating the removal of said element. It should be realized that the grip portion may have any suitable configuration. For example, it could be oval instead of circular, or it could be constituted by a lug or a tongue extending over a part of the circumference, only.

The stroke of the plunger determining the amount of liquid to be sucked into the device may also be defined by surmountable stops located on the inside wall of the device. The stops may be formed by circumferential beads or may be formed by inner sleeves extending from the end opposite the expel end and being e g ultrasonically welded to the inside wall of the device, at least in some locations.

The device is in particular suited for oral administration to an animal, especially a horse, in particular of an aqueous gel containing a formulation of omeprazole or another proton pump inhibitor or a similar composition. However, it should be evident to the man skilled in the art that the use of the device is not restricted to this field, since it can be used for mixing various kinds of pharmaceutical compositions with other agents, and for oral, rectal or any other suitable administration to many different kinds of living beings, including humans.

It should also be noted that a pharmaceutical composition in the sense of this application does not solely mean a drug, also other kinds of beneficial agents, for instance essential nutrients are intended to be included by this expression.

We claim:

1. A syringe for storing a pharmaceutical composition in a dry state and for mixing the composition with fluid prior to delivery, the syringe comprising:

a hollow body having an outlet sealed by a removable closure;

a plunger displaceably accommodated in the hollow body and in sealing contact with an inner wall of the hollow body;

a chamber defined by the plunger, the inner wall of the hollow body, and the removable closure, the chamber for storing the pharmaceutical composition;

a filling conduit communicating with the chamber through an inlet port located on an interior surface of the chamber;

actuating means for displacing said plunger, said actuating means comprising a tubular rod integral with the plunger, said tubular rod having an inner room forming a filling compartment for storing the fluid and having gradation lines for measuring the fluid in said filling compartment, said filling compartment communicating with said filling conduit; and a check valve for permitting fluid flow into the chamber but preventing fluid flow out of the chamber, the check valve comprising a diaphragm disposed in the chamber and covering the inlet port on the interior surface of the chamber, the diaphragm having one or more slits cut therein, the diaphragm covering and sealing the inlet port and having a portion lying against the interior surface of the chamber adjacent to the inlet port when the flap is at rest, and the diaphragm constructed of a resilient material that will deflect when subjected to a force and return to an original state after termination of the force, wherein the diaphragm deflects inwardly into the chamber when subjected to an inwardly directed force causing an opening in diaphram at the slits, and wherein the interior surface of the chamber adjacent to the inlet inhibits the diaphragm from deflecting outwardly.

2. A syringe according to claim 1, wherein the combined length of said actuating means and said plunger is longer than the hollow body such that a part of said plunger protrudes out of said outlet when said actuating means is fully depressed, thus permitting complete emptying of said chamber.

3. A syringe according to claims 1 or 2, characterized in that an O-ring is provided for accomplishing said sealing contact between said hollow body and said plunger.

4. A syringe according to any of claims 1–2, wherein said conduit is provided in said plunger.

5. A syringe according to claim 4, wherein the end of said tubular rod remote from said plunger is closed by a moisture proof seal.

6. A syringe according to claim 5, wherein said closure is a removable lid.

7. A syringe according to claim 6, wherein said removable closure is a rupturable or a tear-off closure.

8. A syringe according to claim 7, wherein said diaphram is disposed on said plunger.

9. A syringe according to claim 8, wherein said sealing contact between said hollow body and said plunger is accomplished by a sealing means integral with said diaphragm.

10. A syringe according to any of claims 1–2, wherein said chamber is prefilled with said pharmaceutical composition and the syringe is enclosed in a moisture proof envelope, comprising at least one moisture barrier.

11. A syringe according to claim 10, wherein said at least one moisture barrier is comprised by an aluminium layer.

12. A syringe according to any of claims 1–2, wherein said pharmaceutical composition is constituted by enteric coated pellets of a proton pump inhibitor such as omeprazole pellets mixed with a dry gelforming agent.

13. A process for preparing a pharmaceutical preparation by mixing a pharmaceutical, preferably dry and granular, composition with a, preferably fluid, agent shortly before the administration thereof to a living being, comprising the following steps:

filling said composition into the chamber of the syringe according to any of claims 1 or 2;

closing the chamber with a closure;

storing said device until time of use;

providing the fluid agent in said filling conduit;

expanding the chamber by displacing said plunger to create a vacuum in the chamber and open the check valve, thereby transferring said agent to said chamber;

optionally, shaking said device until said preparation is formed;

providing an opening to said chamber by removing said closure when said preparation is to be administered;

expelling said preparation from said device by displacing said plunger towards said opening.

14. A method for oral administration of a pharmaceutical preparation, which is achieved by mixing a preferably dry and granular, composition with a preferably fluid agent, said composition being contained in the chamber of the syringe according to claims 1 or 2, the method comprising the steps of:

providing the fluid agent in said filling conduit;

displacing said plunder away from said outlet thereby creating a vacuum in said chamber and thus causing the check valve to open so that said fluid agent is aspirated into said chamber in a quantity adapted to the amount of composition in said chamber;

optionally shaking said device until said preparation is formed;

removing the closure lust before administration of said preparation;

inserting said device with said outlet located where the preparation is to be placed; and expelling said preparation by displacing said plunger towards said outlet.

* * * * *